United States Patent [19]

Derderian et al.

[11] 4,171,910
[45] Oct. 23, 1979

[54] RETROREFLECTANCE MEASUREMENT SYSTEM

[75] Inventors: George Derderian, Maitland; Denis R. Breglia, Altamonte Springs, both of Fla.

[73] Assignee: The United States of America as represented by the Secretary of the Navy, Washington, D.C.

[21] Appl. No.: 789,161

[22] Filed: Apr. 20, 1977

[51] Int. Cl.² .................... G01B 9/00; G01B 11/30
[52] U.S. Cl. .................................. 356/124; 356/371; 356/400
[58] Field of Search ............... 356/120, 124, 210–212, 356/399–401; 250/224, 548

[56] References Cited

U.S. PATENT DOCUMENTS

| | | | |
|---|---|---|---|
| 1,507,212 | 9/1924 | Silberstein | 350/233 |
| 3,406,292 | 10/1968 | Geier et al. | 356/171 |
| 3,448,280 | 6/1969 | Blitchington et al. | 250/224 |
| 3,761,179 | 9/1973 | Plummer et al. | 356/120 |
| 3,892,494 | 7/1975 | Baker et al. | 356/120 |
| 3,975,102 | 8/1976 | Rosenfeld et al. | 356/120 |
| 4,097,751 | 6/1978 | Egan et al. | 356/447 |

OTHER PUBLICATIONS

Zurasky, J. L. "Cube Corner Retroreflector Test and Analysis" App. Optics, 2-1976, pp. 445–452.

Primary Examiner—John K. Corbin
Assistant Examiner—Wm. H. Punter
Attorney, Agent, or Firm—Richard S. Sciascia; Robert W. Adams; David S. Kalmbaugh

[57] ABSTRACT

A retroreflector evaluation system is disclosed as incorporating a laser and a plurality of laser light processing optical elements associated therewith in such manner as will permit the making of reflectance measurements at any or all points on the surface of retroreflective or other reflective samples or devices, thereby providing an indication of the intensity, uniformity, and other reflectance characteristics which determine the quality thereof.

15 Claims, 2 Drawing Figures

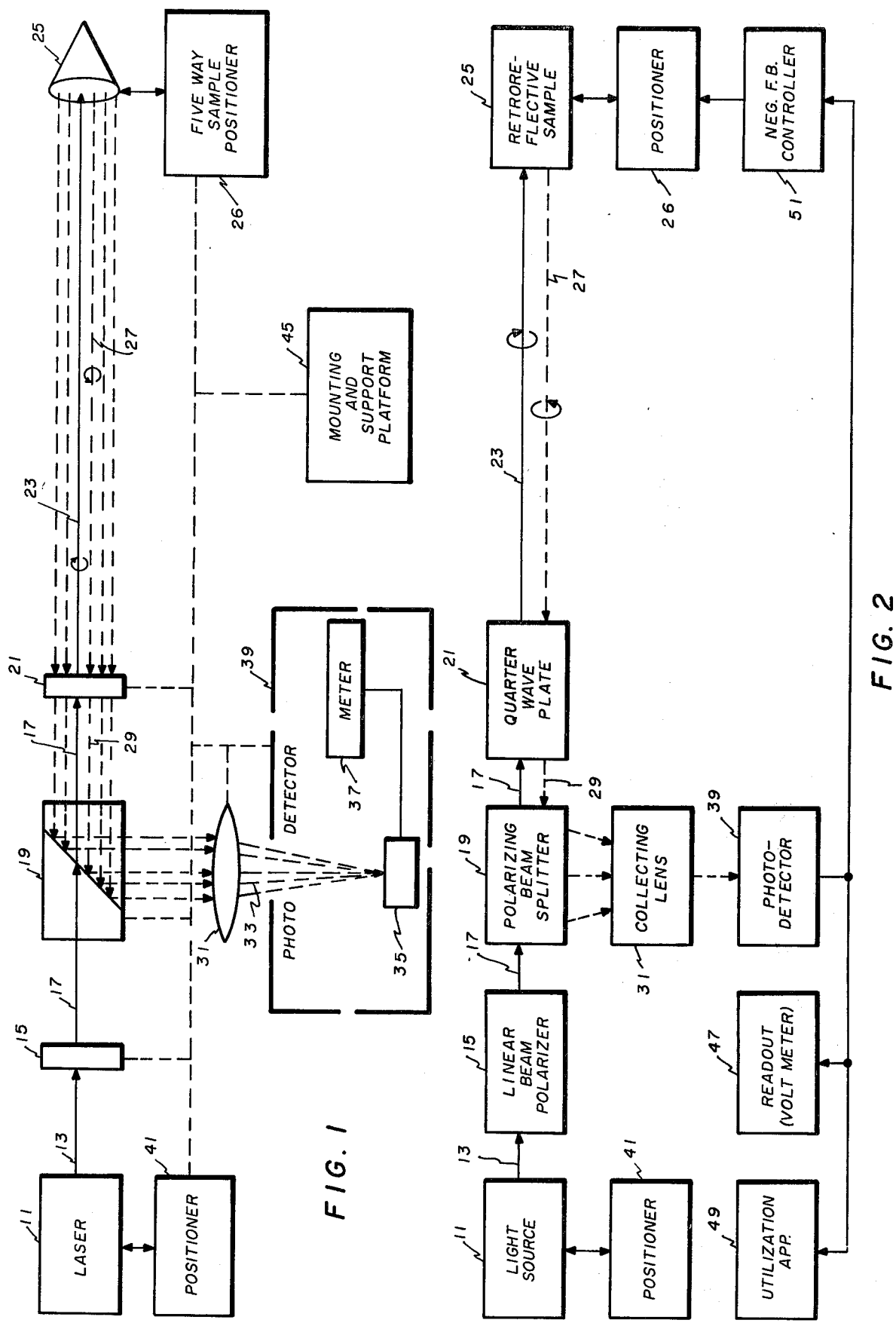

RETROREFLECTANCE MEASUREMENT SYSTEM

FIELD OF THE INVENTION

The present invention, in general, relates to optical testing instruments and, in particular, is an instrument for testing and evaluating the reflecting characteristics of a retroreflector. In even greater particularity, the subject invention is an improved method and means for calibrating the light reflection capabilities of any light reflecting surface.

DESCRIPTION OF THE PRIOR ART

Heretofore, reflectance measurement systems have not had the capability of measuring on-axis or near-on-axis reflections from reflective surfaces. Hence, the accuracies of such measurements leave something to be desired.

SUMMARY OF THE INVENTION

Briefly, the subject invention comprises a new and unique optical system for measuring the reflectance of retroreflectors and other radiant energy reflectors with considerable accuracy and with considerable versatility. Incorporated therein are a plurality of optical elements which permit the making of relative reflectance measurements at all points on the surface of a reflective sample as a function of incident angles, thereby, in turn, providing a calibration of the quality and iniformity of the reflectance thereof.

Therefore, an object of the present invention is to provide an improved method and means for measuring and calibrating the reflectance characteristics of a retroreflective object.

Another object of the invention is to provide an improved reflectance measuring instrument for measuring on-axis and near on-axis reflectance from a light reflective sample.

Still another object of this invention is to provide an improved method and means for ascertaining the light reflection characteristics of a corner cube type retroreflector.

A further object of this invention is to provide a light reflectance measuring instrument with unlimited attitude mounting of the reflector being tested.

Another object of this invention is to provide an improved transmitter-receiver configuration for scoring hits when used as a laser weapon firing similator against retroreflective targets.

Other objects and many of the attendant advantages of this invention will be readily appreciated as the same becomes better understood by reference to the following detailed description when considered in connection with the accompanying drawing wherein:

BRIEF DESCRIPTION OF THE DRAWING

FIG. 1 is a combination functional—schematic—block diagram of the system constituting the instant invention;

FIG. 2 is a generalized block diagram of another species of the subject invention.

DESCRIPTION OF THE PREFERRED EMBODIMENTS

Referring now to both FIGS. 1 and 2, wherein like elements are referenced by like reference numerals, there is shown a light source 11, which is preferably a monochromatic light source, the light of which has a wavelength that corresponds to the wavelength at which it is desired to test the reflection characteristics of a retroreflector. In even greater particularity, light source 11 may be a laser which emits a narrow beam 13 of light with a high degree of collimation aong a predetermined optical or light path.

Disposed along laser light path 13 is a polarizer 15, the function of which is to linearly polarize the laser beam from laser 11 in some predetermined direction, say, in the vertical direction, and disposed in the path 13 thereof is a polarizing beam splitter 19, the latter of which has the ability to transmit light of one linear polarization while reflecting light linearly polarized orthogonally thereto (in this case, through an angle of 90°). Polarizing beam splitter 19, in this instance, is oriented in such manner that it will transmit most of the incident vertical polarized light 17 directly therethrough (thus, still referenced as 17) and, at the same time, reflects at 90° with respect to said direct beam the redirected horizontal polarized light incident thereon, as will be discussed more fully subsequently.

A quarter wave plate 21, having a wavelength specific to the wavelength of the light produced by laser 11, is spatially disposed along the path of direct laser light beam 17 after it has passed through the aforesaid polarizing beam splitter 19. Quarter wave plate 21 is characterized by its ability, when properly oriented, to change vertically polarized light into right circularly polarized light and left circularly polarized light into horizontally polarized light. Hence, as depicted in FIG. 1, the vertically polarized light 17 that passes directly through polarizing beam splitter 19 becomes right circularly polarized light 23 as it emerges from quarter wave plate 21, and that is the light that impacts upon or is incident retroreflector 25 being tested or calibrated for its reflection characteristics at various predetermined points on the reflective surface thereof. With respect to the reflection points being tested, it may be noteworthy that retroreflector 25 may be positioned as desired by any suitable, conventional five-way sample positioner 26, such as, for instance, a plurality of translation tables and rotation mounts, or the like, so that the incident beam 23 can be made to strike any position on the retroreflector's surface with any desired angle of incidence. Of course, in order to obtain such situations, positioner 26 is manually or otherwise adjustable from the position standpoint. Thus, the net result is that each point of interest on the surface of retroreflector 25 can be exposed to incident light 23 from a variety of incident angles.

The on-axis or near on-axis retroreflected beam 27—a plurality of which is represented as being typical in FIG. 1, but only one in FIG. 2—emerges from retroreflector 25 parallel to but slightly displaced from incident beam 23 for reasons which will be explained shortly. This reflected beam 27 is now a left circularly polarized beam (because of its propagation reversal caused by its reflection by retroreflector 25, the retroreflector being examined), and it is this left circularly polarized beam 27 that passes through the aforesaid quarter wave plate 21 in the direction reverse that of direct beam 17. As it passes through quarter wave plate 21, left circularly polarized beam 21 becomes horizontally polarized beam 29—or, in the alternative, it becomes polarized in a direction that is normal to that of the aforesaid beam 17, in the event beam 17 was polarized at some polarization direction other than vertical.

Horizontally polarized beam 29 is reflected through, say, 90° by polarizing beam splitter 19 into a collecting lens 31, which, in turn, focuses and redirects the light 33 thereof to a photodiode or photocell 35, the output of which is connected to the input of any suitable readout meter 37 or other apparatus (not shown in FIG. 1), as desired.

As previously mentioned, because retroreflected beam 27 emerges parallel to but may be slightly displaced from direct beam 23 after it has been reflected from retroreflector 25, such displacement makes it necessary that the aperture dimensions of polarizing beam splitter 19, quarter wave plate 21, and collecting lens 31 be twice the aperture dimension of sample retroreflector 25, so as to optimize the response thereto thereby. Also, in order for lens 31 to focus the light collected thereby to the proper focal point, the focal length thereof is preferably twice the diameter thereof, with the diameter thereof being proportional to the size of retroreflector 25, as mentioned above.

As depicted in FIG. 1, when combined, photocell 35 and meter 37 become photodetector 39 (in both FIGS. 1 and 2). Of course, any other photodetector may be substituted for photodetector 39, if so doing would enhance the operation for any given operational purpose. Thus, for instance, the Powermeter Model 900 type of photodetector manufactured by the Coherent Optics Corporation of Fairport, New York may be employed as photodetector 39, if so desired.

In the event it is necessary or desirable to position laser 11 at some predetermined position with "fine tuning," any conventional positioner 41 may optionally be used therefor; and because it is necessary to change the position and attitude of retroreflector 25 in order to measure the reflectance of the entire reflective surface thereof, say, the previously mentioned five way sample positioner 26 of any suitable conventional type is connected thereto. For example, the aforementioned positioners 26 and 41 may include any of the stackable and-/or rotatable tables manufactured by Kinamatic Ardel Instrument Company, Inc., of Jamaica, New York.

Although not so disclosed in FIG. 2, all of the elements of FIG. 1 are mounted on and supported by a mounting and support platform 45, either directly or indirectly, with the relative dispositions thereof thereon being such as will facilitate the measurement of the reflectance of the retroreflector 25 being calibrated. Obviously, it would be well within the purview of the artisan having the benefit of the teachings presented herewith to design platform 45 and mount all of the aforesaid elements thereon in whatever manner as would effect the optimum operation thereof; hence, the details thereof are not deemed to be necessary.

As illustrated in FIG. 2, so as to disclose the subject invention without limitation, any appropriate readout 47—such as, for example, a voltmeter or the like—calibrated in useful reflectance measurement terms and any other utilization apparatus 49 may be optionally connected to the output of photodetector 39 if so doing would be pertinent to and useful for any given operational purposes. Of course, if warranted by the respective structure thereof, the aforementioned readout 47 and utilization apparatus 49 may also be effectively connected to the output of collecting lens 31 for response to the light or other radiant energy transmitted thereby.

In addition, should it be desirable for any reason to automatically position retroreflective sample 25 while it is being tested or calibrated with respect to reflectance characteristics, a negative feedback control system 51 of any appropriate conventional type may be effectively connected between the output of the photocell of photodetector 39 and the input of positioner 26 for control purposes.

MODE OF OPERATION

The operation of the instant invention is really quite simple, yet the results produced thereby are quite valuable. Accordingly, the operation thereof will now be discussed briefly in conjunction with both figures of the drawing.

The narrow collimated beam of monochromatic light 13 (or other radiant energy, depending on the reflector being tested) is directed by laser 11 through polarizer 15 which polarizes it vertically, so that it becomes vertically polarized light beam 17. This linearly polarized beam 17 then passes through polarizing beam splitter 19 without being changed, and then it passes through quarter wave plate 21, which causes it to be converted to right circularly polarized laser light 23 before it impacts upon and is reflected by retroreflector 25. As previously suggested, right circularly polarized light 23 becomes left circularly polarized light 27 after it has had its propagation direction reversed as a result of its having been reflected from retroreflector 25, with the latter being parallel to but slightly displaced from the former. Left circularly polarized light 27 then passes back through quarter wave plate 21 in a direction that is the reverse from the direction of travel of direct laser light 23, and as a consequence thereof, becomes horizontally polarized (or polarized at a direction that is 90° with respect to the direction of polarized light 17, in the event the latter was not previously polarized in the vertical direction) as horizontally polarized light 29, a plurality of rays of which is shown in FIG. 1 for the purpose of displaying like representative reflection measurement points. Then horizontally polarized beam 29 is reflected 90° by the aforementioned polarizing beam splitter 19, due to its inherent characteristics of passing or transmitting one linearly polarized light while reflecting light that is polarized orthogonally with respect thereto, and then it is collected and focused on photodiode 35 by means of collector lens 31. The intensity of the light focused on photodiode 35 is proportional to the reflectance of retroreflector 25 at the particular point thereon that right circularly polarized light 23 is impacting- —and, thus, being reflected from —at that moment. Obviously, the greater the intensity of light received thereby, the greater the output voltage therefrom; and the greater the output voltage from photodiode 35, the higher the reading on meter 37 or readout 47, as the case may be. Then, when meter 37 or readout 47 are calibrated in terms of reflectance and the indicia thereon indicates such, reflectance values may be obtained for any point on the reflective surface of retroreflector 25.

As previously mentioned, other utilization apparatus may be actuated or enabled by any given output signal level from photodiode 35 or photodetector 39; and, also, the control of retroflector 25 (or the reflection intensity therefrom) may be accomplished with reflectance as the sensed parameter thereof, if so desired, as disclosed in the generalized system embodiment of FIG. 2.

In view of the foregoing, it may readily be seen that the quality, quantity, and uniformity of reflectance from sample reflectors and retroreflectors may be readily determined and indicated or recorded with considerable accuracy, the latter of which is, of course, contingent upon the accuracy of a reference surface of known reflectance characteristics used for the calibration of the entire invention.

Obviously many modifications and variations of the present invention are possible in the light of the above teachings. It is, therefore, to be understood that within the scope of the appended claims the invention may be practiced otherwise than as specifically described.

What is claimed is:

1. A retroreflectance measuring instrument for measuring reflectance of an object, comprising in combination:
   means for projecting a collimated monochromatic first light beam along a predetermined light path;
   means spatially disposed from said collimated monochromatic first light beam projecting means on the aforesaid predetermined light path for polarizing the first light beam projected thereby as a second light beam that is polarized in a first linear direction;
   means spatially disposed from said first linear direction polarizing means on said predetermined light path for directly passing said linearly polarized second light beam received therefrom and for reflecting a third light beam received from the opposite direction that has been polarized in a second linear direction that is orthogonal to the aforesaid first linear direction at a predetermined angle with respect to the aforesaid predetermined light path;
   means spatially disposed from the aforesaid polarized light beams passing and reflecting means on said predetermined light path and adapted to provide a right circularly polarized fourth light beam to the object and to receive a left circularly polarized fifth light beam reflected from the object, for converting the aforesaid linearly polarized second light beam into the right circularly polarized fourth light beam as it travels downstream therethrough and for converting the left circularly polarized fifth light beam into the aforesaid orthogonally linearly polarized third light beam as it travels upstream therethrough toward the reflecting surface of the aforesaid polarized light beams passing and reflecting means;
   means spatially disposed from said polarized light beams passing and reflecting means for collecting and focusing the linearly polarized third light beam reflected thereby at a given focal point;
   means effectively disposed at said focal point for sensing and reading out said reflected linearly polarized third light beam in terms of reflectance units;
   means adapted to be connected to the object for effecting the positioning thereof at any predetermined location and attitude with respect to the aforesaid predetermined light path; and
   means effectively connected to said collimated monochromatic first light beam projecting means for positioning said collimated monochromatic first light beam projecting means at a predetermined location and attitude with fine tuning.

2. The device of claim 1, wherein said means for projecting a collimated monochromatic first light beam along a predetermined light path comprises a laser.

3. The device of claim 1, wherein said means spatially disposed from said collimated monochromatic first light beam projecting means on the aforesaid predetermined light path for polarizing the first light beam projected thereby as a second light beam that is polarized in a first linear direction comprises a polarizer that polarizes said second light beam in the vertical direction.

4. The device of claim 1, wherein said means spatially disposed from said first linear direction polarizing means on said predetermined light path for directly passing said linearly polarized second light beam received therefrom and for reflecting a third light beam received from the opposite direction that has been polarized in a second linear direction that is orthogonal to the aforesaid first linear direction at a predetermined angle with respect to the aforesaid predetermined light path comprises a polarizing beam splitter.

5. The device of claim 1, wherein said means spatially disposed from the aforesaid polarized light beams passing and reflecting means on said predetermined light path and adapted to provide a right circularly polarized fourth light beam to the object and to receive a left circularly polarized fifth light beam reflected from the object, for converting the aforesaid linearly polarized second light beam into the right circularly polarized fourth light beam as it travels downstream therethrough and for converting the left circularly polarized fifth light beam into the aforesaid orthogonally linearly polarized third light beam as it travels upstream therethrough toward the reflecting surface of the aforesaid polarized light beams passing and reflecting means comprises a quarter wave plate disposed at a predetermined angle with respect to the aforesaid predetermined light path.

6. The device of claim 1, wherein said means spatially disposed from said polarized light beams passing and reflecting means for collecting and focusing the linearly polarized third light beam reflected thereby at a given focal point comprises a collector lens.

7. The device of claim 1, wherein said means effectively disposed at said focal point for sensing and reading out said reflected linearly polarized third light beam in terms of reflectance units comprises a photodetector.

8. The invention of claim 1, further characterized by a means effectively connected to each of the aforesaid means for the mounting and supporting thereof in predetermined relative positions.

9. The invention of claim 1, further characterized by a retroreflector spatially disposed from said light beam converting means for reflecting said right circularly polarized fourth light beam as the aforesaid left circularly polarized fifth light beam.

10. The invention of claim 1, further characterized by means spatially disposed from said light beam converting means on the aforesaid predetermined light path for reflecting the light received therefrom.

11. The invention of claim 1, further characterized by a negative feedback controller connected between an output of said means for sensing and reading out and an input of said means for effecting positioning for controlling said means for effecting positioning in accordance with a predetermined set position.

12. A retroreflectance measuring system, comprising in combination:
   a laser for broadcasting a monochromatic collimated light beam along a first light path;
   a linear polarizer spatially disposed downstream from said laser on said first light path;
   a polarizing beam splitter, having a direct downstream polarized light transmission capability along said first light path and a reflective transmission capability along a second light path that is located at a predetermined angle with respect to said first light path for redirected upstream polarized light that is polarized orthogonally with respect to the aforesaid direct downstream polarized light;

a quarter wave plate spatially disposed directly downstream from said polarizing beam splitter on said first light path;

a retroreflector spatially disposed downstream of said quarter wave plate with the reflective surface thereof facing substantially upstream along said first light path and toward the downstream side of said quarter wave plate;

a five way sample positioner effectively connected to said retroreflector for adjusting the position of said retroreflector within a predetermined plurality of degrees of freedom;

a collector lens spatially disposed from the aforesaid polarizing beam splitter in such manner as to collect and focus the light reflected thereby at a point on a predetermined second light path;

a photodetector spatially disposed from said collector lens on said second light path at a location contiguously disposed with the aforesaid collector lens focal point; and a positioner effectively connected to said laser for positioning said laser at a predetermined location and attitude with fine tuning so as to permit the varying of the light path of the monochromatic collimated light beam broadcast by said laser.

13. The invention of claim 12, further characterized by means effectively connected to said laser, linear polarizer, polarizing beam splitter, quarter wave plate, retroreflector, collector lens, and photodetector for the positioning of each thereof in predetermined relative dispositions with respect to each of the others.

14. The device of claim 12, wherein said photodetector spatially disposed from said collector lens on said second light path at a location contiguously disposed with the aforesaid collector lens focal point comprises:
a photocell; and
a meter calibrated in units of reflectance connected to the output of said photocell.

15. The invention of claim 12, further characterized by a negative feedback controller connected between an output of said photodetector and an input of said means for adjusting position, for controlling the disposition of said retroreflector in accordance with a predetermined set position.

* * * * *